United States Patent [19]

Emde et al.

[11] 4,435,336

[45] Mar. 6, 1984

[54] PROCESS FOR THE PREPARATION OF AROMATIC AMINOSULPHONIC ACIDS

[75] Inventors: Herbert Emde, Cologne; Heinz U. Blank; Peter Schnegg, both of Odenthal, all of Fed. Rep. of Germany

[73] Assignee: Bayer Aktiengesellschaft, Leverkusen, Fed. Rep. of Germany

[21] Appl. No.: 364,082

[22] Filed: Mar. 31, 1982

[30] Foreign Application Priority Data

Apr. 11, 1981 [DE] Fed. Rep. of Germany ....... 3114829

[51] Int. Cl.³ .................. C07C 143/58; C07C 143/60
[52] U.S. Cl. .................................... 260/508; 260/509; 260/396 R; 260/374; 260/373; 260/371; 546/195; 546/203; 546/204; 546/205; 546/206; 548/400; 548/529; 548/577

[58] Field of Search ............... 260/508, 509, 371, 373, 260/374, 396 R; 546/195, 203, 204, 205, 206; 548/577, 529, 400

[56] References Cited

PUBLICATIONS

Alexander, JACS, 69, 1599 (1947).

*Primary Examiner*—Nicky Chan
*Attorney, Agent, or Firm*—Sprung, Horn, Kramer & Woods

[57] ABSTRACT

Aminoarylsulphonic acids which have a relatively high purity and a relatively low content of aminoaryldisulphonic acids can be obtained, if they are prepared, from the corresponding arylammonium hydrogen sulphates, by an improved version of the so-called baking process, wherein the reaction is carried out under pressure at a temperature of at least 140° C. and, at least partially, in the presence of water.

17 Claims, No Drawings

PROCESS FOR THE PREPARATION OF AROMATIC AMINOSULPHONIC ACIDS

The present invention relates to a process for the preparation of aminoarylsulphonic acids by the so-called baking process from an arylamine and sulphuric acid.

It is already known that aromatic aminosulphonic acids are obtained at an elevated temperature from an arylamine and sulphuric acid (Helv. Chim. Acta 15, 1372 (1932)). In a first stage of this so-called baking process the corresponding arylammonium hydrogen sulphate is formed, which then reacts, in bulk or in an inert solvent, at an elevated temperature with the elimination of water to give the corresponding aminosulphonic acid. To increase the rate of the reaction and to complete the reaction desired, the resulting water is in general removed, alone or, when a solvent is used, together with it, from the reaction mixture as rapidly and as completely as possible, usually with a vacuum being applied (BIOS, 11536, page 175, page 182 and 188 and Ind. Eng. Chem. 42, 1746 (1950)). This procedure produces aminoaryldisulphonic acids and isomeric aminoarylsulphonic acids as undesirable byproducts and products which are frequently dark-coloured (Russian Pat. No. 667,550). In addition, long reaction times are required, whilst yields are moderate (Ind. Eng. Chem., loc. cit.).

A process has now been found for the preparation of aminoarylsulphonic acids by reacting arylamines with sulphuric acid by the so-called baking process, which is characterized in that the reaction is carried out under pressure at a temperature of at least 140° C. and, at least partially, in the presence of water.

In the process according to the invention, arylamines of the general formula (I)

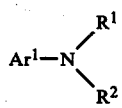   (I)

can be employed,
in which
   $R^1$ and $R^2$ independently of one another denote hydrogen, alkyl, aralkyl or aryl, or both together form, together with the N atom on which they are substituted, a nitrogen-containing heterocyclic structure and
   $Ar^1$ represents an optionally substituted benzene, naphthalene, anthracene, naphthoquinone or anthraquinone skeleton or the skeleton of an aromatic heterocyclic structure.

Examples which may be mentioned of alkyl are those alkyls which have 1 to 8, preferably 1 to 4, and particularly preferably 1 to 2, C atoms, such as methyl, ethyl, propyl, isopropyl, butyl, isobutyl, hexyl or octyl.

Examples which may be mentioned of aralkyl are benzyl, 1-phenylethyl, 2-phenylethyl, naphthylmethyl, naphthylethyl, anthrylmethyl and anthrylethyl, preferably benzyl.

Examples which may be mentioned of aryl are phenyl, substituted phenyl, naphthyl and diphenyl, preferably phenyl.

In the event that $R^1$ and $R^2$ together form, together with the N atom on which they are substituted, a nitrogen-containing heterocyclic structure, examples which may be mentioned of the latter are those which have 4 to 8, preferably 5 or 6, ring members, such as pyrrolidine or piperidine.

A substituted benzene, naphthalene, anthracene, naphthoquinone or anthraquinone skeleton can have, in addition to an amino group $-NR^1R^2$, for example, up to 3 further substituents, preferably up to 2 substituents, the substituents being so located that at least one ortho- or para-position is unsubstituted. Examples which may be mentioned of substituents are alkyl, within the scope of the abovementioned range of meaning, trifluoromethyl, and perfluoroethyl; examples of further substituents are phenyl, alkoxy having 1 to 4, preferably 1 to 2, C atoms, for example methoxy, ethoxy, propoxy, isopropoxy, butoxy or isobutoxy, alkylthio, such as thio analogues of the alkoxy groups mentioned, halogen, such as fluorine, chlorine or bromine, and also hydroxyl, nitro, optionally substituted amino, $SO_3H$ and carboxyl, and also alkylsulphonyl and arylsulphonyl, such as methylsulphonyl, ethylsulphonyl or phenylsulphonyl. Preferred substituents which may be mentioned are methyl, ethyl, phenyl, methoxy, ethoxy, halogen, hydroxyl, nitro and amino. Very particularly preferred substituents which may be mentioned are methyl, chlorine, bromine, fluorine, methoxy and ethoxy.

Preferred arylamines which can be used according to the invention are those of the formula (II)

   (II)

in which
   $Ar^1$ has the meaning mentioned and
   $R^3$ and $R^4$ independently of one another represent hydrogen or alkyl.

Particularly preferred arylamines for the process according to the invention are those of the formula (III)

   (III)

in which
   $Ar^1$ has the meaning mentioned.

Further preferred arylamines for the process according to the invention are those of the formula (IV)

   (IV)

in which
   $R^1$ and $R^2$ have the abovementioned meaning and
   $Ar^2$ represents the benzene or naphthalene skeleton.

Further particularly preferred arylamines for the process according to the invention are those of the formula (V)

   (V)

in which
   $R^3$, $R^4$ and $Ar^2$ have the meaning mentioned.

Arylamines of the formula (VI)

$$Ar^2-NH_2 \quad (VI)$$

in which

Ar$^2$ has the meaning mentioned and represents in particular the benzene skeleton, are employed very particularly preferably.

Examples of arylamines which can be used in the process according to the invention are aniline, o-toluidine, m-toluidine, p-toluidine, 2,4-dimethylaniline, 2,3-dimethylaniline, 2,6-dimethylaniline, 2,5-dimethylaniline, N-methylaniline, N-ethylaniline, N,N-dimethylaniline, diphenylamine, p-chloroaniline, 2,4-dichloroaniline, o-chloroaniline, 2,3-dichloroaniline, 3,5-dichloroaniline, 2,5-dichloroaniline, 2,6-dichloroaniline, m-chloroaniline, 2-amino-6-chlorotoluene, 2-amino-5-chlorotoluene, 2-amino-4-chlorotoluene, 2-methoxy-5-methylaniline, p-methoxyaniline, o-nitroaniline, m-nitroaniline, p-nitroaniline, α-naphthylamine, p-phenylenediamine, m-phenylenediamine, aminodiphenyl, p-nitrodiphenylamine, 2-methoxy-4-nitroaniline, 1-amino-2-ethoxynaphthalene, 1-amino-2-hydroxynaphthalene, 1-amino-8-hydroxynaphthalene, 1-amino-5-hydroxynaphthalene, 1,8-diamino-naphthalene, 1,5-diaminonaphthalene, 2-amino-3-hydroxynaphthalene, 2-aminopyridine, 3-chloro-4-methoxyaniline, 2-aminobenzoic acid, p-ethoxyaniline, 3,4-dichloroaniline, o-fluoroaniline, m-fluoroaniline, p-fluoroaniline, 2-amino-3-chlorotoluene, 3-amino-2-chlorotoluene, 5-amino-2-chlorotoluene, 3-amino-5-chlorotoluene, 3-amino-4-chlorotoluene, 4-amino-3-chlorotoluene, 4-amino-2-chlorotoluene, 5-methoxy-2-methylaniline, 2,3-, 2,4-, 2,5-, 2,6-, 3,4-, 3,5-dimethoxy- and diethoxyaniline, o-methoxyaniline, m-methoxyaniline, N-acetyl-p-phenylenediamine, 2-chloro-4-methoxyaniline, 2-chloro-3-methoxyaniline, 4-chloro-3-methoxyaniline, 5-chloro-3-methoxyaniline, 2-chloro-5-methoxyaniline, 3-chloro-2-methoxyaniline, 4-chloro-2-methoxyaniline, 5-chloro-2-methoxyaniline, 2-chloro-6-methoxyaniline and also analogous chloroethoxyanilines, 3-amino-6-chlorobenzoic acid, o-trifluoromethylaniline, m-trifluoromethylaniline, p-trifluoromethylaniline, aminoanthraquinones, such as, for example, 1-aminoanthraquinone or 1,5-diaminoanthraquinone, benzidine and dehydrothiotoluidine.

An arylamine is reacted with sulphuric acid in a ratio of 0.5 to 1.1, preferably 0.90 to 1.05, and particularly preferably 0.95 to 1.02, mols of sulphuric acid per mol of amine, if appropriate in the presence of an additional alkali metal hydrogen sulphate. Sulphuric acid and amine are very particularly preferably reacted in a molar ratio of about 1:1. However, it is also possible to employ the corresponding arylammonium hydrogen sulphates in a solid form, as a suspension or as a melt, in the process according to the invention.

Sulphuric acid can be employed in the form of concentrated sulphuric acid (the so-called monohydrate) or as dilute sulphuric acid. An H$_2$SO$_4$ content of 70 to 100% by weight may be mentioned as an example. However, it is also possible to employ sulphuric acid which contains free dissolved sulphur trioxide, for example 0.5 to 65% by weight, relative to this SO$_3$-containing sulphuric acid. In a case such as this, the number of mols of sulphuric acid and of SO$_3$ are counted together for the purpose of calculating the abovementioned molar quantity of H$_2$SO$_4$ per mol of amine. Sulphuric acid containing 70 to 100% by weight, particularly 96 to 100% by weight, of H$_2$SO$_4$ is preferably employed, and monohydrate is very particularly preferably employed.

According to the invention, it is possible to work without or with a solvent. The procedure in which a solvent is used is preferable. In the event that the procedure involving the presence of a solvent is used, alkyl- and/or halogen-substituted aromatics may be mentioned as suitable examples. Examples of what may be understood here are benzene, naphthalene, anthracene or diphenyl, which can carry up to 4 alkyl groups and/or up to 4 halogen atoms, such as fluorine, chlorine or bromine, as substituents, the total number of substituents being of course limited to the total number of positions on the basic aromatic entity which can be substituted. Examples which may be mentioned of alkyl substituents are those which have 1 to 4, preferably 1 to 2, and preferably, 1 C atom(s), such as methyl, ethyl, propyl, isopropyl, butyl or isobutyl. It is also possible for two adjacent alkyl substituents together to form an alkylene chain having 3 to 5 C atoms, such as trimethylene, tetramethylene or pentamethylene.

Examples of such solvents are toluene, xylene, trimethylbenzene, ethylbenzene, methylnaphthalene, tetrahydronaphthalene, methylanthracene, methyldiphenyl, fluorobenzene, chlorobenzene, bromobenzene, 1,2-dichlorobenzene, 1,3-dichlorobenzene, 1,4-dichlorobenzene, 1,2-dibromobenzene, 1,3-dibromobenzene, 1,4-dibromobenzene, 1,2-, 1,3-, 1,4-difluorobenzene, trifluoromethylbenzene, chlorinated biphenyls, mono- and/or polychlorinated naphthalene, 1,2,4-trichlorobenzene, 1,2,3-trichlorobenzene, 1,3,5-trichlorobenzene, 2-chlorotoluene, 3-chlorotoluene, 4-chlorotoluene, 2-bromotoluene, 3-bromotoluene, 4-bromotoluene, 2,6-dichlorotoluene, 2,4-dichlorotoluene, 2,5-dichlorotoluene, 2,3-dichlorotoluene and 3,4-dichlorotoluene. These solvents can be used not only on their own but also in a mixture, for example in the form of a technical dichlorobenzene mixture, dichlorotoluene mixture or trichlorobenzene mixture. However, it is also possible to use as solvents aliphatic hydrocarbons, such as paraffin oil, kerosene or paraffins, such as isododecane or decalin, and also mixtures thereof which have suitable boiling points. Preferred solvents are alkyl- and/or halogen-substituted benzenes, in which the total number of substituents is of course limited to a maximum of 6. Benzenes which are substituted by 1 to 3 halogen atoms and which can additionally carry one methyl group are employed particularly preferably. Dichloro- and/or trichlorobenzenes and/or -toluenes are employed very particularly preferably; 1,2-dichlorobenzene, 1,2,4-trichlorobenzene and the technical mixture of dichlorotoluenes may be mentioned here by way of example.

The solvent is used in an amount of 100 to 2,000 ml, preferably 100 to 500 ml, per mol of arylamine.

The arylammonium hydrogen sulphate which is obtainable on combining an arylamine and sulphuric acid, if appropriate in one of the solvents mentioned, is then reacted according to the invention under pressure at a temperature of at least 140° C. and, at least partially, in the presence of water, to give the corresponding aminoarylsulphonic acid.

The temperature may be mentioned as being in general 140° to 280° C., preferably 150° to 260° C. and particularly preferably 180° to 250° C.

The process according to the invention can be carried out continuously or discontinuously in, for example, reactors, such as autoclaves, pressure vessels, all-phase reactors or reactors of the paddle-dryer type.

The pressure to be set according to the invention is chosen from the range between the partial vapour pressure of the solvent under the conditions of the process and the highest possible pressure of the reaction system. The highest possible pressure of the reaction system is that pressure which becomes established in the closed reactor and it depends on the reaction temperature, the nature of the solvent and the extent of the reaction. It is of course possible to inject into the reaction system, in addition to the pressure establishing itself, an inert gas, such as nitrogen or noble gases.

A range from 1.01 to 50 bar, preferably 1.05 to 20 bar and particularly preferably 1.1 to 10 bar may be mentioned as an example of the pressure.

According to the invention, the reaction of an arylammonium hydrogen sulphate to give the corresponding aminoarylsulphonic acid is carried out at least partially in the presence of water. An example of what the expression "at least partially" is understood as meaning here, is the way in which that part of the reaction is carried out in which 10 to 100%, preferably 50 to 100%, and particularly preferably 70 to 100%, of the total conversion of the reaction are achieved. It is of course also possible to carry out that part of the reaction in which, respectively, 0 to 10%, or 0 to 50%, or 0 to 70%, of the total conversion is achieved in the presence of water. An example which may be mentioned of the amount of water which is present according to the invention in the reactor during the course of the so-called baking process is 0.01 to 2 mols, preferably 0.02 to 0.5 mol and particularly preferably 0.02 to 0.2 mol, of water per mol of arylamine originally introduced into the reaction mixture. At least some of this water can be reaction water resulting in the baking process. However, it can also be water which has been additionally added to the batch, for example by employing water-containing sulphuric acid. Water which is present in the reaction mixture and the amount of which exceeds the quantities indicated is not detrimental at the start of the process according to the invention. However, such excess quantities of water are distilled off in the further course of the reaction of the process according to the invention. Even water which is present, in accordance with the invention, during the reaction is completely removed from the reaction mixture before the end of the reaction. The removal of water during the course of the reaction of the process according to the invention can be effected in a continuous or discontinuous manner, so that the reaction mixture still contains towards the end of the reaction only an amount of water which is in the lower part of the abovementioned range. This makes it possible that the moment at which water has been removed completely approximately coincides with the end of the reaction.

The process according to the invention can be carried out, for example, by introducing an arylamine and sulphuric acid, and a solvent which, if appropriate, is also used, and water which, if appropriate, is additionally also used within the scope of the above description, in optional sequence, into a pressure vessel. There is no need here to take special measures concerning the increased temperature which arises due to the exothermic neutralisation reaction between the arylamine and sulphuric acid. The pressure vessel is then closed and raised to a temperature of at least 140° C. Water is then removed continuously or batchwise from the reaction batch, if desired after a short starting-up phase of the reaction, at a rate which is such that an amount of water which is within the scope of the above description always remains in the reaction batch. Some of the solvent also being used may also distil over together with the water being distilled from the pressure reactor. This solvent which has distilled over can be separated from water in a water separator and passed back in a suitable way into the pressure reactor. By controlling in a suitable manner the pressure under which distillate is removed, it can be ensured that water present in the reaction mixture is never removed completely therefrom. In principle it is also possible to carry out the condensation and the separation of water and co-distilled solvent under the pressure prevailing in the reactor. This is done by passing possibly co-distilled solvent in a technically simple manner back into the reactor via a water separator which is under the reaction pressure. It is of course also possible to maintain the amount of water which, according to the invention, is required to be present in the reaction mixture, by a continuous feed into the reaction mixture, for example via a pump.

In another variant of the process according to the invention the mixture resulting from the addition of the reactants and, if desired, solvent and, if desired additionally added water is heated under atmospheric pressure and while water is being distilled off at the same time, until the conversion of the baking has reached 10%, preferably 50%, and particularly preferably 70%, of the total coversion. This can also result in a temperature being reached which is already at 140° C. or above. The reactor is only closed at that point, and the process is continued in the manner which has already been described above and with application of the desired pressure, for example of the intrinsic pressure (autogenous) of the reaction mixture.

The reaction mixture obtained after complete conversion can be worked up in various ways, if appropriate after it has been cooled down to below 100° C. In the event that a solvent was used, it is possible, for example, to separate the aminoarylsulphonic acid which is not or only sparingly soluble in the solvent from the solvent by filtering it off or by centrifuging. However, the reaction mixture can also be subjected to an alkaline-aqueous extraction, in which an aminoarylsulphonic acid transfers, in the form of its salt, into the aqueous phase. Examples of substances which have an alkaline reaction and can be used in such an alkaline-aqueous extraction are sodium hydroxide, potassium hydroxide, calcium hydroxide, magnesium hydroxide, sodium carbonate, potassium carbonate, calcium carbonate, magnesium carbonate, ammonia and aliphatic amines. Sodium hydroxide or potassium hydroxide are preferably used. In the event that the reaction was carried out in the presence of a solvent, the aqueous extract is then advantageously freed from traces of the solvent by incipient distillation. The clear, almost colourless salt solution, thus obtainable, of the aminoarylsulphonic acid can in general be employed without any further purification. However, if desired, this aqueous phase can also be treated with suitable adsorbents, such as active charcoal or polymeric organic adsorbing agents. However, this aqueous extract can also be worked up by evaporating it to leave an aminoarylsulphonic acid salt which corresponds to the alkaline compound used. Furthermore, this extract can also be treated by acidifying it with a mineral acid, such as hydrochloric acid or sulphuric acid, which precipitates a free, very pure aminoarylsulphonic acid which can be isolated, for example by filtration.

With the aid of the process according to the invention, a very pure aminoarylsulphonic acid can be prepared in yields of over 95%. The resulting aminoarylsulphonic acid contains, in particular, very small amounts of undesirable aminoaryldisulphonic acid, isomeric aminoarylsulphonic acids and may contain unreacted amine, which contents are very low, and in general are in each case lower than 2.0% by weight, preferably lower than 0.5% by weight, of the compounds mentioned. Aminoarylsulphonic acids which can be obtained according to the invention furthermore represent a particularly pale product, for example as expressed by the Hazen colour number of a 20% strength by weight aqueous sodium aminoarylsulphonate solution. For example, for p-sulphanilic acid prepared according to the invention this Hazen colour number is about 4 or less, whilst it is at least 13 for the product prepared according to the state of the art. This fact is of great importance, for example, for the use of aminoarylsulphonic acids in the preparation of optical brighteners.

A further advantage of the process according to the invention is that, owing to the application of pressure, the choice of possible solvents is very large. In addition, on carrying out the take-off of water from the reaction mixture under pressure, only an extremely small amount of solvent is distilled off at the same time, in comparison to the baking process under atmospheric pressure or in vacuo, whereby the energy costs of the process can be kept low.

This lastmentioned advantage, of the small amount of solvent which is co-distilled in the process according to the invention, is intended to be demonstrated, by way of example, by means of the tabular comparison which follows. All the data refer to a baking of 2.5 mols of anilinium sulphate in which at most 45 ml of reaction water are produced. Bakings, in o-dichlorobenzene and in 1,2,4-trichlorobenzene, carried out according to the state of the art (1 bar) and according to the invention (a typical overpressure at the start and the end of the H$_2$O distillation is indicated) and also the amount of co-distilled solvent, the ratio by volume of H$_2$O:solvent, and the temperature, are compared.

| Solvent | Number of ml distilled | H$_2$O: solvent | Pressure (bar) | Temperature (°C.) |
| --- | --- | --- | --- | --- |
| Dichlorobenzene | 6,750 | 1:150 | 1 | 180 |
| Dichlorobenzene | 50 | 1:1.1 | 2.4 to 1.6 | 200 |
| Trichlorobenzene | 850 | 1:19 | 1 | 190 to 210 |
| Trichlorobenzene | 29 | 1:0.64 | 7.9 to 1.3 | 240 |

According to the hitherto prevalent thinking on the course of the so-called baking process and the way it should be carried out, it appeared to be necessary to remove the reaction water formed in the conversion of an arylammonium hydrogen sulphate into the corresponding aminoarylsulphonic acid from the reaction mixture completely and as speedily as possible, in order to push the reaction into the direction of the aminoarylsulphonic acid. It was been found, surprisingly, that contrary to this prevailing opinion the baking process can be advantageously carried out in the presence of water, leading to products which have a lighter colour and contain fewer undesirable byproducts.

Aminoarylsulphonic acids which can be obtained in the process according to the invention are valuable intermediate products in the preparation of pharmaceuticals, foamed plastics, optical brighteners, wetting agents, synthetic mordants, tanning agents, resist agents, insecticides, finishing agents, softeners and polymeric thickeners (Ullmanns Enzyklopädie der technischen Chemie [Ullmann's Encyclopaedia of Industrial Chemistry], 3rd edition, volume 16, page 561, Verlag Urban and Schwarzenberg, Munich/Berlin 1965).

EXAMPLE 1

(for comparison)

(according to the method of B. I. Kissin, E. N. Kurakin, Khim. Prom. 41, 104 (1965))

186.2 g (2 mols) of aniline are initially introduced into 500 ml of 1,2-dichlorobenzene and 208.3 g (2.04 mols) of 96% strength sulphuric acid are added dropwise. The mixture is heated for 8 hours at the boil under a water separator, during which period distillate passes over at a rate of 700 ml per hour, cooled and filtered with suction. After it has been dried, the precipitate weighs 338.5 g and contains 86.1% of p-sulphanilic acid (84.2% of the theoretical yield) and 11.2% of aniline-2,4-disulphonic acid (7.5%, relative to aniline).

EXAMPLE 2

651.7 g (7.0 mols) of aniline are initially introduced into 1,400 ml of 1,2-dichlorobenzene in a 4 l enamel stirred autoclave, and 686.7 g (7.0 mols) of monohydrate are added. The autoclave is closed and heated to an internal temperature of 200° C. 122 ml of water are removed via a valve together with 140 ml of solvent, in the course of 2.75 hours, during which period the initial pressure of 2.4 bar drops to 1.6 bar. After cooling down to 120° C., the suspension is filtered hot with suction and it yields a residue weighing 1,203 g after drying. The content in this residue of p-sulphanilic acid is 98.0% by weight and of aniline-2,4-disulphonic acid 0.5% by weight. This is calculated to be a yield of p-sulphanilic acid of 97.2% of the theoretical yield. The Hazen colour number of a 20% strength aqueous sodium salt solution is 3.

EXAMPLE 3

(for comparison)

(according to B. I. Kissin, USSR Patent No. 667,550).

150 g (1.61 mols) of aniline are initially introduced into a mixture of 310 ml of 1,2-dichlorobenzene and 62 ml of 1,2,4-trichlorobenzene. 160 g (1.63 mols) of monohydrate are added dropwise in the course of 60 minutes, during which period the temperature rises to 123° C. The mixture is heated to the boil, (172° C.), and 28 ml of water and 186 ml of solvent mixture are distilled off in the course of 8 hours, during which period the temperature rises up to 182° C., and heating is then continued for a further 6 hours under a water separator. A dark, viscous suspension is obtained. Residual solvent is distilled off in a water jet vacuum (154 ml), 450 ml of water are added to the residue, and the resulting mixture is neutralised with 120 ml of 40% strength NaOH. The solution is freed from black residues by filtering it with suction, a steam distillation is then carried out for 1 hour, and the residue is evaporated to dryness. The grey residue weighs, after drying, 295 g and contains 84.9% by weight of p-sulphanilic acid (89.8% yield, relative to aniline, or 88.7%, relative to H$_2$SO$_4$, and 2.2% by weight of aniline-2,4-disulphonic acid). Hazen colour number of a 20% strength aqueous sodium salt solution=13.

EXAMPLE 4

470.1 g (5.05 mols) of aniline are initially introduced into 1,000 ml of 1,2,4-trichlorobenzene in a stirred autoclave, and 490 g (5.0 mols) of monohydrate are added dropwise in the course of 15 minutes. The internal temperature of the closed autoclave is raised to 240° C., and reaction water (90 ml) containing small amounts of solvent (58 ml) is removed by continuously letting down and condensing over 40 minutes, the initial pressure being 7.8 bar which falls, after the valve has been opened, to 3.2 bar and further falls in the course of the reaction to a pressure of 1.3 bar. Stirring is continued for a further 50 minutes at this temperature and under a pressure of 1.3 bar. 3,100 ml of water and 374 ml of a 50% strength potassium hydroxide solution are then added, the phases are separated, and 460 ml are distilled off from the aqueous phase. The aqueous potassium salt solution then weighs 4,218.5 g and contains 20.1% by weight of p-sulphanilic acid (98% of the theoretical yield). The content of aniline-2,4-disulphonic acid is 0.054% by weight. The Hazen colour number of a 20% strength sodium salt solution is 4.

EXAMPLE 5

470.1 g (5.05 mols) of aniline are initially introduced into 1,000 ml of dichlorotoluene in a stirred autoclave, and 490 g (5.0 mols) of monohydrate are added dropwise in the course of 30 minutes. The temperature rises to about 150° C. The mixture is heated to 210° C., and reaction water containing a small amount of solvent is continuously removed at this temperature and under an initial pressure of 2.1 bar. The removal of reaction water is complete after about 60 minutes, and stirring is continued for a further 30 minutes under a pressure of 1.2 bar. The reaction batch is worked up as in Example 4. 1,014.2 g of potassium salt of p-sulphanilic acid (98.4% pure) are obtained. The content of p-sulphanilic acid is 80.7% (94.5% of the theoretical yield), and the content of aniline-2,4-disulphonic acid is 1.0%.

EXAMPLE 6

305.6 g (3.28 mols) of aniline are initially introduced into 650 ml of 1,2-dichlorobenzene in a 2 l glass autoclave. 318.8 g (3.25 mols) of monohydrate are added dropwise with stirring under atmospheric pressure in the course of 10 minutes, during which period the temperature rises to 154° C. The autoclave is fitted with a control valve which opens automatically at a differential pressure of 1.3 bar and is heated to an internal temperature of 200° C. The resulting reaction water is distilled off via the control valve together with small amounts of solvent. After 2 hours about 56 ml of water (of a theoretically possible amount of 58.5 ml) have been distilled off together with 80 ml of solvent. Stirring is continued for a further 1 hour in the closed autoclave. The resulting suspension is filtered with suction and the flter residue is dried. Isolated p-sulphanilic acid has a weight of 556.3 g and a content of 99.5% by weight; the content of aniline-2,4-disulphonic acid is about 0.4% by weight. The yield is 98.3%, relative to sulphuric acid.

EXAMPLE 7

214 g (2.0 mols) of o-toluidine are initially introduced into 1,000 ml of 1,2-dichlorobenzene in a 3 l enamel autoclave, and 196.2 g (2.0 mols) of monohydrate are added under atmospheric pressure. The autoclave is closed and heated to an internal temperature of 200° C., the pressure increasing to 3.1 bar. The reaction water is distilled off via a valve together with small amounts of solvent, the pressure dropping to 1.1 bar. After 1.5 hours the reaction water (34 ml) has been distilled off together with 40 ml of 1,2-dichlorobenzene. The suspension is filtered with suction, and the filter residue weighs 371.6 g after drying. The content of 4-amino-3-methylbenzenesulphonic acid is 99.6% by weight, which corresponds to a yield of 99% of the theoretical yield. The content of unreacted toluidine is about 0.2% by weight.

EXAMPLE 8

286.4 g (2.0 mols) of α-naphthylamine are initially introduced into 1,000 ml of 1,2-dichlorobenzene in a 3 l enamel stirred autoclave, and 196.2 g (2.0 mols) of monohydrate are added. The addition is complete after 15 minutes. The autoclave is closed and heated to 190° C., the pressure increasing to 3 bar. After a reaction time of 2.5 hours 33 ml of reaction water have been distilled off via a valve together with 60 ml of solvent. The granular suspension is extracted with aqueous sodium hydroxide solution, which leaves unreacted α-naphthylamine in the organic phase and re-usable for a subsequent batch. The aqueous phase is evaporated to dryness, leaving 465.6 g of p-naphthionic acid (90.1% pure), which corresponds to a yield of 92.0% of the theoretical yield.

EXAMPLE 9

255.2 g (2.0 mols) of p-chloroaniline are initially introduced into 1,000 ml of 1,2-dichlorobenzene in a 3 l enamel stirred autoclave, and 196.2 g (2.0 mols) of monohydrate are added under atmospheric pressure. The autoclave is heated up with the valve in the open position. As distillation sets in, the valve is closed to an extent which is such that the amount of distillate remains small and the desired reaction temperature of 200° C. is reached. 32 ml of reaction water are then distilled off continuously together with 90 ml of solvent under a maximum pressure of 1.6 bar. The suspension is filtered hot with suction. The precipitate weighs 412.9 g after drying and contains 98% by weight of 2-amino-5-chlorobenzenesulphonic acid, which corresponds to a yield of 97.5% of the theoretical yield.

EXAMPLE 10

255.2 g (2.0 mols) of o-chloroaniline are initially introduced into 1,000 ml of 1,2-dichlorobenzene in a stirred autoclave, and 196.2 g (2.0 mols) of monohydrate are added. The mixture is heated to 200° C., and 33 ml of reaction water are distilled off via a 2 mm valve in the course of 1.5 hours, during which period only 40 ml of solvent are also distilled off. The initial pressure of 2.4 bar drops to 1.6 bar towards the end of the reaction. The suspension is filtered with suction and the precipitate is dried. The solid weighs 417.4 g and has a content of 98.5% by weight of 4-amino-3-chlorobenzene sulphonic acid and 0.1% by weight of o-chloroaniline. The yield is 99.0% of the theoretical yield.

EXAMPLE 11

324.2 g (2.0 mols) of 3,4-dichloroaniline are initially introduced into 1,000 ml of 1,2-dichlorobenzene in a 3 l enamel stirred autoclave. 196.2 g (2.0 mols) of monohydrate are added dropwise in the course of 10 minutes, and the entire batch is heated to 205° C. with the autoclave in a closed position. 33 ml of reaction water are distilled off via a valve in the course of 1 hour and 50 minutes together with only 50 ml of solvent, during which period the pressure drops from 2.5 bar to 1.2 bar. The precipitate obtained after filtering with suction weighs 477.6 g after drying and contains 96.9% by weight of 2-amino-4,5-dichlorobenzenesulphonic acid; this corresponds to 95.6% of the theoretical yield.

EXAMPLE 12

283.2 g (2.0 mols) of 3-chloro-4-methylaniline are initially introduced into 1,000 ml of 1,2-dichlorobenzene in a 3 l enamel stirred autoclave, and 196.2 g (2.0 mols) of monohydrate are added in the course of 7 minutes. The closed autoclave is heated to 200° C., a pressure of 2.8 bar becoming established. 35 ml of reaction water are then distilled off together with 80 ml of solvent in the course of 1 hour and 25 minutes, during which period the pressure drops to 1.3 bar. After filtering with suction and drying, 440.8 g of 2-amino-4-chloro-5-methylbenzenesulphonic acid, which is 99.5% by weight pure, remain. This corresponds to 99.0% of the theoretical yield.

EXAMPLE 13

283.2 g (2.0 mols) of 4-chloro-3-methylaniline are reacted as described in Example 12 with 196.2 g (2.0 mols) of monohydrate. After a distillation of 1.5 hours via a 2 mm valve, 130 ml of solvent are obtained in addition to 34 ml of reaction water. During the distillation the pressure drops from 2.5 bar to 1.3 bar. The purity of dry 2-amino-5-chloro-4-methylbenzenesulphonic acid (438.5 g) is 99.0%, which corresponds to a yield of 98.0% of the theoretical yield.

EXAMPLE 14

324.2 g (2.0 mols) of 2,3-dichloroaniline are dissolved in a mixture of 880 ml of 1,2-dichlorobenzene and 120 ml of chlorobenzene, and 196.2 g (2.0 mols) of monohydrate are added. The closed autoclave is heated for 1 hour at 175° C. and for a further hour at a temperature within the range from 180° to 190° C. During this period 34 ml of water and 250 ml of solvent are distilled off and the initial pressure of 2.3 bar drops to 1.3 bar. After filtering with suction and drying, 476.1 g of 99% pure 2-amino-3,4-dichlorobenzenesulphonic acid are obtained, which corresponds to 97.3% of the theoretical yield.

What is claimed is:

1. In a process for the preparation of an aminoarylsulphonic acid by heating a reaction mixture comprising an arylamine and sulphuric acid or an arylammonium hydrogen sulphate by the baking process, the improvement which comprises carrying out the process under pressure at a temperature of at least 140° C. and, at least partially, in the presence of water, sulphuric acid where present being present in an amount of 0.5 to 1.1 mols per mol of arylamine, said water being present in the reaction mixture in an amount of 0.02 to 2 mols per mol of arylamine or arylammonium hydrogen sulphate originally introduced into the reaction mixture.

2. A process according to claim 1, wherein the process is carried out in the presence of a solvent.

3. A process according to claim 2, wherein the process is carried out within a pressure range between the partial vapor pressure of the solvent under the conditions of the process and the highest possible pressure of the reaction system.

4. A process according to claim 1, wherein the process is carried out at a temperature in the range of 140° to 280° C.

5. A process according to claim 4, wherein the process is carried out at a temperature of 150° to 260° C.

6. A process according to claim 1, wherein the arylamine is one of the formula

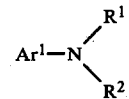

wherein
$R^1$ and $R^2$ independently of one another denote hydrogen, alkyl, aralkyl or aryl, or both together form, together with the N atom on which they are substituted, a nitrogen-containing heterocyclic structure and
$Ar^1$ represents an optionally substituted benzene, naphthalene, anthracene, naphthoquinone or anthraquinone skeleton or the skeleton of an aromatic heterocyclic structure.

7. A process according to claim 1, wherein said aryl amine is one of the formula

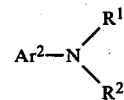

wherein
$R^1$ and $R^2$ independently of one another denote hydrogen, alkyl, aralkyl or aryl, or both together form, together with the nitrogen atom on which they are substituted, the nitrogen-containing heterocyclic structure and
$Ar^2$ represents the benzene or naphthalene skeleton.

8. A process according to claim 1, wherein said arylamine has the formula $Ar^2$—$NH_2$ wherein $Ar^2$ represents the benzene or naphthalene structure.

9. A process according to claim 1, wherein water is added to the reaction mixture.

10. A process according to claim 1, wherein an arylammonium hydrogen sulphate is heated in the presence of a solvent.

11. A process according to claim 1, wherein the process is carried out in the presence of water obtained by the heating at elevated temperature of said arylamine together with sulphuric acid or by the heating of said arylammonium hydrogen sulphate.

12. A process according to claim 11, wherein the process is carried out by the addition of water to the reaction mixture.

13. A process according to claim 1, wherein the process is carried out in the presence of 0.02 to 0.5 mol of water per mol of arylamine or arylammonium hydrogen sulphate originally introduced into the reaction mixture.

14. A process according to claim 1, wherein the process is carried out in the presence of 0.02 to 0.2 mol of water per mol of arylamine or arylammonium hydrogen sulphate originally introduced into the reaction mixture.

15. A process according to claim 1, wherein said sulphuric acid is present in an amount of 0.95 to 1.02 moles per mole of arylamine.

16. A process according to claim 1, wherein said water includes water which has been added to the reaction mixture.

17. A process according to claim 1, wherein the reaction mixture consists essentially of said arylamine and sulphuric acid or arylammonium hydrogen sulphate and water.

* * * * *